United States Patent [19]

Kremer, Jr.

[11] Patent Number: 4,803,977
[45] Date of Patent: Feb. 14, 1989

[54] METHOD AND APPARATUS FOR THE DIAGNOSIS OF RESPIRATORY DISEASES AND ALLERGIES

[75] Inventor: Carl P. Kremer, Jr., Darien, Conn.
[73] Assignee: Mallinckrodt, Inc., St. Louis, Mo.
[21] Appl. No.: 30,595
[22] Filed: Mar. 27, 1987

Related U.S. Application Data

[60] Division of Ser. No. 838,197, Mar. 7, 1986, Pat. No. 4,660,547, which is a continuation of Ser. No. 736,519, May 20, 1985, abandoned, which is a continuation of Ser. No. 608,563, May 9, 1984, abandoned, which is a continuation of Ser. No. 361,767, Mar. 25, 1982, abandoned.

[51] Int. Cl.$^4$ .............................................. A61B 6/00
[52] U.S. Cl. ....................................... 600/3; 128/654; 128/200.21; 128/200.18; 128/898
[58] Field of Search ..................... 128/1.1, 654, 200.14, 128/200.15, 200.16, 200.17, 200.18, 200.19, 200.21, 200.22, 203.13, 203.12

[56] References Cited

U.S. PATENT DOCUMENTS

| | | | |
|---|---|---|---|
| 2,840,074 | 6/1958 | Serda | 128/188 |
| 3,863,630 | 2/1975 | Cavallo | 128/145.6 |
| 3,976,050 | 8/1976 | Glasser et al. | 128/2 A |
| 4,094,317 | 6/1978 | Wasnich | 128/200.16 |
| 4,113,809 | 9/1978 | Abair et al. | 128/81 |
| 4,116,387 | 9/1978 | Kremer, Jr. et al. | 128/200.18 |
| 4,174,712 | 11/1979 | Monren et al. | 128/173 R |
| 4,177,945 | 12/1979 | Schwartz et al. | 239/338 |
| 4,251,033 | 2/1981 | Rich et al. | 128/200.18 |
| 4,256,100 | 3/1981 | Levy et al. | 128/204.21 |
| 4,510,929 | 4/1985 | Bordoni et al. | 128/200.14 |
| 4,598,704 | 7/1986 | Bordoni et al. | 128/200.14 |
| 4,660,547 | 4/1987 | Kremer, Jr. | 128/1.1 |

OTHER PUBLICATIONS

Michael Hayes, M.D. et al, "Improved Radioaerosol Emboli Administration System for Routine Inhalation Lung Imaging", Journal of Radiology, 4/79.

Nichols et al., "Detection of Pulmonary Emboli by Position Imaging of Inhaled O-Labeled Carbon Dioxide", Seminars in Nuclear Medicine, vol. X, No. 3, Jul. 1980.

Michael Hayes for George Taplin, "Lung Imaging with Radioaerosols for the Assessment of Airway Disease", Seminars in Nuclear Medicine, vol. X, No. 3, Jul. 1980.

Primary Examiner—Edward M. Coven
Assistant Examiner—J. P. Lacyk
Attorney, Agent, or Firm—Bernard, Rothwell & Brown

[57] ABSTRACT

Method and apparatus for coating the airways of the lung of a patient substantially uniformly with a mist formed by aspirating a liquid which includes restricting the maximum size of the particles of the mist to about 1.2 microns with the major portion of the particles being in the range of 0.056 microns to 1 micron causing the mist to behave as a gas, conduits for feeding the mist together with a gas containing oxygen to a patient to be inhaled during the normal breathing process, and valves connected with the conduits for diverting the exhaled mist and gas through a discharge path. By radioactively tagging the liquid prior to production of the mist, the uniform deposition of the mist throughout the entire lung without encountering heavy accumulations in the large airways and at branch points, enables the production of high definition image scans of the lung.

9 Claims, 1 Drawing Sheet

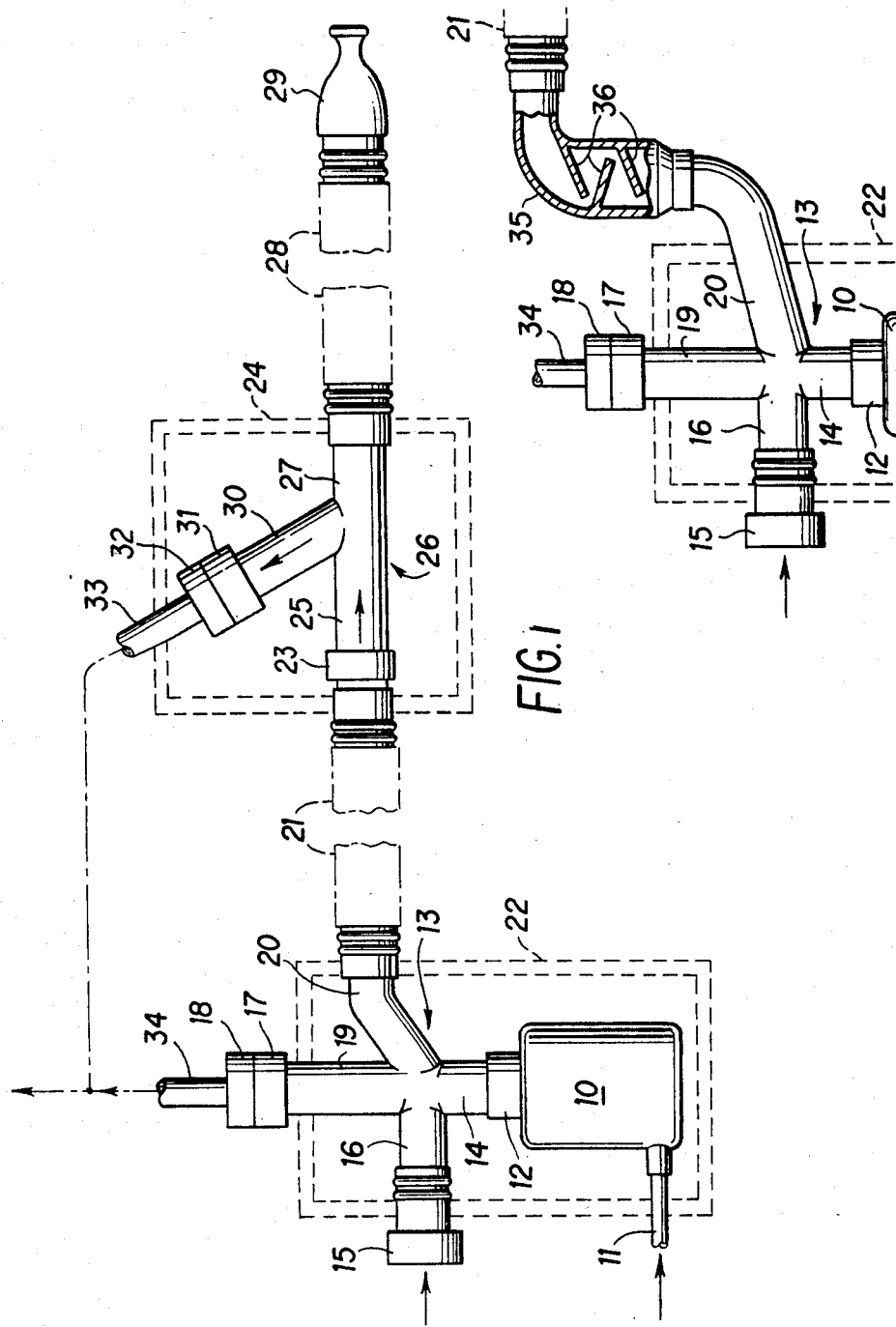

METHOD AND APPARATUS FOR THE DIAGNOSIS OF RESPIRATORY DISEASES AND ALLERGIES

This is a division of application Ser. No. 838,197, filed Mar. 7, 1986, now U.S. Pat. No. 4,660,547, which is a continuation of 736,519 filed May 20, 1985 and now abandoned, which is a continuation of 608,563 filed May 9, 1984 and now abandoned, which is a continuation of 361,767 filed Mar. 25, 1982 and now abandoned.

This invention relates to the diagnosis of respiratory disease and more specifically to a novel and improved method and apparatus utilizing an aerosolized radioactive isotope for ventilation of the lungs to enable the production of multiple images of relatively high resolution and contrast to facilitate location of emboli, tumors and the like as well as other diseases affecting the respiratory tract without the danger of hyperdeposition and loss of image clarity.

Heretofore, diagnosis of respiratory diseases was principally effected by perfusion lung scans and ventilation utilizing radioactive gases. The use of radioactive aerosols was also considered but it was found that with known systems excessive deposition or rainout occurred not only in the upper respiratory tract, the oral pharynx or the trachea but also at airway intersections. Moreover, uneven deposition of the mist was observed between the central and peripheral areas of the lung. Accordingly, when ventilation scans are deemed desirable, radioactive gases such as xenon and krypton are generally relied upon notwithstanding the relatively high cost entailed in producing the gas, patient inconvenience, extremely limited time in which to obtain even one image of the lung and the need for containment and disposition of the exhaled gas.

This invention overcomes the problems heretofore entailed in the diagnosis of lung diseases and provides a method and apparatus utilizing a radioactive mist which avoids the difficulties entailed with gases as well as the problems heretofore encountered with aerosols. More specifically, it has been found that with the utilization of aerosols wherein the particle size is maintianed below approximately 1.2 microns with by far the major portion of the particles being well below 1 micron, the mist behaves much the same as a gas and does not produce material rainout or hyperdeposition in the upper respiratory tract, pharynx or trachea. Moreover, there is substantially uniform deposition throughout the entire lung without accumulation at airway branching points and the patient can be in any position and is not required to hold his breath during the scanning operation and ample time is available for multiple scans. Furthermore, the isotope being in aerosol form can, upon being exhaled, be filtered out and safely stored until the radioactivity reaches a safe level for convenient disposition. Radioactive gases however cannot be filtered and great care is required for containment and storage, the latter requiring extended periods of time as compared to aerosols.

Another object of the invention resides in the provision of a novel and improved method and apparatus for the diagnosis of lung diseases characterized by its simplicity, reliability, ease of operation and relatively low cost.

Still another object of the invention resides in the provision of novel and improved diagnostic apparatus which enables multiple photographic views of the lung to be recorded with little if any patient inconvenience.

A still further object of the invention resides in the provision of a novel and improved method and apparatus for making image ventilation studies of the lung which affords greatly improved resolution and contrast.

The invention utilizes a nebulizer wherein the maximum particle size is essentially limited to 1.2 microns with a negligible quantity of particles larger than 1.2 microns. A unidirectional air inlet is coupled to the output of the nebulizer and the output is also coupled through a unidirectional flow valve and a T- or Y-connector to a mouthpiece or face mask through which the patient inhales the mist produced by the nebulizer. The third or discharge opening on the connector includes a unidirectional flow valve for the discharge of mist and air exhaled by the patient and a filter for the removal of the radioactive mist. The output from the filter is preferably fed to a suitable container for storage until the radioactivity decays to a safe level for disposal. Since the nebulizer is usually operated continuously by a compressed air supply, means are also provided at the output of the nebulizer to prevent the development of excess pressure during the exhaling periods.

The above and other objects and advantages of the invention will become more apparent from the following description and accompanying drawings forming part of this application.

IN THE DRAWINGS

FIG. 1 is a side elevational view in partially diagrammatic form of one embodiment of apparatus in accordance with the invention; and FIG. 2 is a side elevational view in partially diagrammatic form of a modification of the invention shown in FIG. 1.

While the desirability of utilizing radioactive aerosols or mists for the diagnosis of lung diseases had been suggested because of convenience and relatively low cost, the procedure has not heretofore been utilized because of excessive deposition of the aerosols in large airways, posterior pharynx, trachea, stomach and the like. It was also generally considered that a satisfactory radioactive mist must merely not include particles larger than 2 microns in mean mass aerodynamic diameter. With the invention now to be described, it has been found that particle sizes not only should not exceed 1.2 microns but that the particles of the aerosol should be in the range of about 0.056 microns to about 1.2 microns with approximately 90% of the particles being under 1 micron. Under these conditions, the aerosol behaves as a gas and the desired objectives can be achieved.

In preparation of the aerosol for the production of radioactive scans, either $^{99m}$technetium-sulphur colloid or $^{99m}$technetium-diethylene triamine penta-acetate functioned satisfactorily and have half lives of about 6 hours which provides adequate time for multiple image scans and yet a short enough half life to provide for convenient disposal. Gases not only require the patient to hold his breath during an image scan which affords time for only a single scan but known satisfactory gases such as krypton has a half life of less than 30 seconds making it difficult to provide time for even the single scan and forms of tagged Xenon have half lives of from 4 to 30 days making disposal difficult. The radioactive technetium compounds referred to above are generally available in Nuclear Medicine Departments for routine clinical diagnostic procedures and accordingly constitute a relatively inexpensive and available aerosol for the conduct of ventilation scans.

Referring now to FIG. 1 showing a partially diagrammatic elevational view of one form of apparatus in accordance with the invention, the nebulizer is generally denoted by the numeral 10 and includes a compressed gas inlet 11 and an outlet 12. The nebulizer may take any desired form though in the illustrated embodiment, the housing would include a suitable reservoir, an aspirator for producing the mist and the gas such as oxygen or air should be supplied at the rate of the order of 6 to 10 liters per minute. In the instant embodiment of the invention, a four-way connector generally denoted by the numeral 13 is coupled to the outlet 12 of the nebulizer 10 by the tubular leg 14. A unidirectional air inlet valve 15 is connected to a second tubular leg 16 of the four-way connector 13, a second unidirectional outlet valve 17 and particle filter 18 are connected to a third leg 19 of the four-way connector 13 and a fourth leg 20 of the connector 13 is connected to flexible tubing 21 having a bellows configuration for delivery of the aerosol to the patient. It is preferable to enclose the nebulizer 10 together with the four-way connector 13 within a container 22 formed of lead or other radiation shielding material since the nebulizer will contain a radioactive liquid.

The outlet end of the tubing 21 is connected to a third unidirectional valve 23 which may be contained within a second container 24 also formed of lead or other radiation shielding material. The outlet of the one-way valve 23 is coupled to one leg 25 of a Y-connector 26 disposed within the container 24 and the second leg 27 of the Y-connector is coupled to a flexible tube 28 similar to that of the tube 21. A mouthpiece 29 for the patient is secured to the end of the tube 28 so that the patient can conveniently inhale the mist generated by the nebulizer 10 together with air entering the one-way valve 15. While a simple mouthpiece 29 has been illustrated, a suitable facemask may replace the mouthpiece if so desired. The unidirectional flow valve 23 may take any desired form and may preferably be adjusted to prevent flow during the presence of atmospheric pressure on the downstream side of the valve and provide for free flow when the downstream pressure is reduced during the time the patient is in the process of inhaling.

When utilizing aerosols for ventilation scans, the patient may inhale and exhale several times in order to be certain that the radioactive mist has been uniformly deposited throughout the entire lung. During the exhaling periods, the patient will exhale through the mouthpiece or facemask, as the case may be, and through the tube 28. Since the one-way valve 23 will prevent reverse flow of mist, the exhaled aerosol will pass outwardly through the leg 30 of the Y-connector 26, a one-way valve 31 and a filter 32 and the exhaled air and/or gas will be discharged through the tube 33. The filter 32 retains the aerosol exhaled by the patient and contains the filtered aerosol until the level of radioactivity has decreased to a safe level for convenient disposal. During the exhaling period, the valve 23 will remain closed and it is therefore desirable to prevent development of excessive pressure within the tube 21 caused by compressed air entering the inlet 11 of the nebulizer 10. For this purpose, the tubing 21, being in the form of a bellows, will tend to expand and thus limit the pressure. If desired, the one-way valve 17 may be utilized and adjusted to act as a relief valve to limit the maximum pressure in the tube 21. When the relief valve 17 is utilized, an aerosol filter 18 is provided to filter out and contain the aerosol and the remaining gas is discharged through the pipe 34. If desired, pipes 33 and 34 may be coupled together and fed to a holding container which will retain the gaseous material until the radioactivity has decreased to a level permitting normal disposal.

The nebulizer 10 may take any desired form provided however that the aerosol particles generated thereby are within the ranges set forth above. One such nebulizer which will generate a mist meeting the requirements outlined above is illustrated and described in U.S. Pat. No. 4,116,387.

FIG. 2 illustrates a modified embodiment of the invention wherein a large particle trap is included in the event the specific nebulizer 10 utilized may have an excess number of large particles.

In the figures, like numerals have been used to denote corresponding elements in each figure.

In FIG. 2, it will be observed that the leg 20 extending from the four-way connector 13 is curved upwardly and receives the vertical leg of an elbow 35 having a plurality of inclined baffles 36. The horizontal output leg of the elbow 35 is then coupled to the bellows-shaped tubing 21 for delivery of the mist to a patient.

The baffle arrangement contained within the elbow 35 provides a circuitous path for the mist with the result that the larger particles which because of their greater mass will tend to collide with one of the baffles and be removed from the remainder of the aerosol. These larger particles upon reconversion to a liquid will automatically drain back into the nebulizer and enter the liquid reservoir therein. If desired, a separate drain may be employed for returning this liquid directly to the reservoir or to an individual receiver.

The method and apparatus for the production of lung scans utilizing an aerosol has been found to be exceedingly effective not only from the standpoint of reduced costs and convenience for the patient but vastly improved image scans have been obtainable which greatly facilitate diagnosis of precise difficulties involving the entire lung.

While the invention is particularly useful for the production of image scans of the lung, it is of course useful for medication of the lung in the treatment of disease. For instance, the method and apparatus would be useful for treatment of the lung with antimicrobials, antifungals, tagged anticancer drugs and the like. The method and apparatus is also useful for provocative allergy testing to determine the body reaction, for instance, to histamines and antigens such as ragweed and the like.

While only certain embodiments of the invention have been illustrated and described, it is apparent that alterations, changes and modifications may be made without departing from the true scope and spirit thereof.

What is claimed is:

1. A method of diagnosing diseases, comprising:
   (a) continuously producing a radioactive mist having particles that do not exceed about 1.2 microns in diameter with a major portion of the particles being within the range of about 0.056 microns to about 1 micron, by continuously aspirating a radioactive liquid utilizing gas under pressure;
   (b) continuously introducing the radioactive mist into a first conduit through a first inlet therein;
   (c) continuously admitting a gas containing oxygen into the first conduit through a second inlet therein;

(d) continuously mixing the gas containing oxygen with said radioactive mist in said first conduit to form a radioactive aerosol mixture;

(e) passing the radioactive aerosol mixture from the first conduit to a second conduit through a first unidirectional control valve that permits unidirectional flow from the first conduit to the second conduit;

(f) feeding the radioactive aerosol mixture from the second conduit into a patient's airways during the patient's breathing to substantially uniformly distribute the radioactive aerosol mixture throughout the patient's airways and deposit the radioactive mist on surfaces therein;

(g) receiving exhaled aerosol from the patient's airway into the second conduit during the patient's breathing;

(h) passing exhaled aerosol from the second conduit through a second unidirectional flow valve to permit unidirectional flow of exhaled aerosol from inside the second conduit to outside the second conduit with the first unidirectional flow valve preventing exhaled aerosol in the second conduit from passing into the first conduit;

(i) preventing development of excessive pressure within the first conduit while exhaled aerosol is being received into the second conduit during the patient's breathing; and (j) producing radioactive image scans of the patient's airways after depositing the radioactive mist therein.

2. The method of claim 1 further including the step of filtering out large particles from the radioactive aerosol mixture prior to passing the radioactive aerosol mixture from the first conduit to the second conduit.

3. The method of claim 2 wherein the large particles are filtered out of the radioactive aerosol mixture by passing the radioactive aerosol mixture in a circuitous path past a plurality of inclined baffles in a large particle trap so as to remove particles colliding with the baffles by converting the particles that collide with the baffles to a liquid and draining the thus formed liquid into said radioactive liquid being aspirated.

4. The method of claim 1 further including the step of filtering exhaled gas passing from inside the second conduit to outside the second conduit through the second unidirectional flow valve so as to remove radioactive mist from the exhaled gas passing through the second unidirectional flow valve.

5. The method of claim 1 wherein the step of preventing development of excessive pressure within the first conduit includes the step providing an undulating bellows that forms at least a portion of the first conduit.

6. The method of claim 1 wherein the step of preventing development of excessive pressure within the first conduit includes the step of venting excess pressure from the first conduit through a unidirectional relief valve permitting unidirectional flow of gas from inside the first conduit to outside the first conduit.

7. The method of claim 6 further including the step of filtering radioactive mist from gas passing through said relief valve from said first conduit.

8. The method of claim 1 wherein approximately 90% of the mist particles are under 1 micron in size.

9. The method of claim 1 wherein said gas under pressure is applied at a rate of about 6–10 liters per minute.

* * * * *